(12) United States Patent
Yokose et al.

(10) Patent No.: US 8,187,841 B2
(45) Date of Patent: May 29, 2012

(54) METHOD FOR EVALUATING OR SELECTING AGENT FOR PREVENTING OR CURING PHOTODAMAGE OF SKIN

(75) Inventors: Urara Yokose, Haga-gun (JP); Akira Hachiya, Haga-gun (JP); Tsutomu Fujimura, Haga-gun (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/487,080

(22) Filed: Jun. 18, 2009

(65) Prior Publication Data
US 2010/0323347 A1   Dec. 23, 2010

(51) Int. Cl.
*C12P 19/34* (2006.01)

(52) U.S. Cl. ...................................... 435/91.2

(58) Field of Classification Search .................. 435/91.2
See application file for complete search history.

(56) References Cited

FOREIGN PATENT DOCUMENTS

| EP | 1000 613 A2 | 5/2000 |
|---|---|---|
| JP | A-2000-86489 | 3/2000 |
| JP | A-2000-159631 | 6/2000 |
| JP | A-2002-104924 | 4/2002 |
| JP | A-2008-31088 | 2/2008 |

OTHER PUBLICATIONS

Martin et al. eur. J. Dermatol. vol. 18, No. 2, pp. 128-135, Mar.-Apr. 2008.*
Kossodo et al. Photochemistry and Photobiology, vol. 79, No. 1, pp. 86-93, 2004.*
Hachiya et al., The American Journal of Pathology, vol. 174, No. 2, pp. 401-413, Feb. 2009.*
Shih et al., Eur. J. Dermatol. vol. 18, No. 3, pp. 303-307, 2008.*
Shin et al., J. Invest. Dermatol., vol. 124, pp. 315-323, 2005.*
Philips et al.,Bios, vol. 80, No. 1, pp. 20-24, Mar. 2009.*
Bissett, DL et al., "An animal model of solar-aged skin: histological, physical, and visible changes in UV-irradiated hairless mouse skin," Photochem Photobiol 46(3): 367-378 (Sep. 1987), Pergamon Journals Ltd., Exeter, UK.
Brennan, M et al. "Matrix metalloproteinase-1 is the major collagenolytic enzyme responsible for collagen damage in UV-irradiated human skin," Photochem Photobiol 78(1): 43-48 (Jul. 2003), Pergamon Journals Ltd., Exeter, UK.
Brenneisen, P, et al., "Ultraviolet B wavelength dependence for the regulation of two major matrix-metalloproteinases and their inhibitor TIMP-1 in human dermal fibroblasts," Photochem Photobiol 64(5): 877-885 (Nov. 1996) Pergamon Journals Ltd., Exeter, UK.
Brenneisen, P. et al., "Activation of protein kinase CK2 is an early step in the ultraviolet B-mediated increase in interstitial collagenase (matrix metalloproteinase-1; MMP-1) and stromelysin-1 (MMP-3) protein levels in human dermal fibroblasts," Biochem J 365(Pt 1): 31-40 (Jul. 2002), Portland Press Ltd., London, UK.
Contet-Audonneau, Jl et al., "A histological study of human wrinkle structures: comparison between sun-exposed areas of the face, with or without wrinkles, and sun-protected areas," Br J Dermatol 140(6): 1038-1047 (Jun. 1999), Blackwell Science Ltd., Oxford, UK.
Del Bino, S et al., "Ultraviolet B induces hyperproliferation and modification of epidermal differentiation in normal human skin grafted on to nude mice," Br J Dermatol 150(4): 658-667 (Apr. 2004), Blackwell Science Ltd., Oxford, UK.
Hachiya, A et al., "Mechanistic Effects of Long-Term Ultraviolet B Irradiation Induce Epidermal and Dermal Changes in Human Skin Xenografts," Am. J. Pathol. 174: 401-413 (Feb. 2009), Am. Soc. Invest. Path., Bethesda, MD.
Imayama, S, et al., "Ultraviolet-B irradiation deforms the configuration of elastic fibers during the induction of actinic elastosis in rats," J Dermatol Sci, 7(1): 32-38 (Feb. 1994), Elsevier Science Ireland Ltd., Shannon, Ireland.
Reed, MJ, et al., "Inhibition of TIMP1 enhances angiogenesis in vivo and cell migration in vitro," Microvasc Res 65(1): 9-17 (Jan 2003), Academic Press, San Diego, CA.
Dialog File 351, Accession No. 9938268, Derwent World Patents Index English language abstract and patent family for JP-A-2000-86489, published Mar. 28, 2000.
Dialog File 351, Accession No. 10168414, Derwent World Patents Index English language abstract and patent family for JP-A-2000-159631, published Jun. 13, 2000.
Dialog File 351, Accession No. 12510142, Derwent World Patents Index English language abstract and patent family for JP-A-2002-104924, published Apr. 10, 2002.
Dialog File 351, Accession No. 17520862, Derwent World Patents Index English language abstract and patent family for JP-A-2008-31088, published Feb. 14, 2008. Brenneisen, P, et al., "Ultraviolet-B induction of interstitial collagenase and stromelyin-1 occurs in human dermal fibroblasts via an autocrine interleukin-6-dependent loop," FEBS Lett 449(1): 36-40 (Apr. 1999), Elsevier, Amsterdam, The Netherlands.
Laga A. C. and Murphy G. F., "The Translational Basis of Human Cutaneous Photoaging," *The American Journal of Pathology*, 174(2): 357-360 (Feb. 2009), American Society of Investigative Pathology.

* cited by examiner

*Primary Examiner* — Gary Benzion
*Assistant Examiner* — Cynthia Wilder
(74) *Attorney, Agent, or Firm* — Sterne, Kessler, Goldstein & Fox P.L.L.C.

(57) ABSTRACT

A method for evaluating or selecting a substance capable of preventing or curing photodamage of skin is provided. Provided is a method for evaluating or selecting an agent for preventing or curing photodamage of skin, the method including: (A) contacting cells that are capable of expressing TIMP-1 gene or TIMP-1 protein, with a test substance; (B) measuring the expression level of the TIMP-1 gene or the TIMP-1 protein in the cells; (C) comparing the expression level obtained in (B), with the expression level of TIMP-1 gene or TIMP-1 protein in a control group in which the cells capable of expressing TIMP-1 gene or TIMP-1 protein have not been contacted with the test substance; and (D) evaluating or selecting the test substance which increases the expression level of TIMP-1 gene or TIMP-1 protein, as an agent for preventing or curing photodamage of skin, based on the results of (C).

10 Claims, 3 Drawing Sheets
(3 of 3 Drawing Sheet(s) Filed in Color)

METHOD FOR EVALUATING OR SELECTING AGENT FOR PREVENTING OR CURING PHOTODAMAGE OF SKIN

BACKGROUND OF THE INVENTION

1. Field of the Invention

The present invention relates to a method for evaluating or selecting an agent for preventing or curing photodamage of skin.

2. Description of the Invention

In the course of development of cutaneous photodamage, quantitative and qualitative changes are induced in both dermis and epidermis, in which such changes in dermis are especially known. That is, cells producing dermal fibers are reduced in size as well as in number due to chronic exposure to solar rays, which leads particularly to heavy loss of collagen fibers and results in degradation of the dermis and loss of subcutaneous adipose tissue. As a result, morphology of skin is changed due to decreased elasticity and looseness of skin, or increased roughness of skin surface.

In order to elucidate the mechanism of photodamage of the skin, or to evaluate a pharmaceutical product useful for the prevention and cure of adverse effects due to photodamage, a model system which can more satisfactorily reflect the photodamaged skin of human being will be useful.

As a skin model or animal model for photoaging, which is caused by photodamage, a system which is exposed to ultraviolet radiation is mostly generally used, and for example, methods of continuously irradiating the dorsal skin of a hairless mouse or the plantar skin of a rat, with ultraviolet radiation everyday for several weeks (Bissett D L, Hannon D P and Orr T V, Photochem. Photobiol., 46 (3), 367-78 (1987); Imayama S, Nakamura K, Takeuchi M, Hori Y, Takema Y, Sakaino Y and Imokawa G, J. Dermatol. Sci., 7 (1), 32-8 (1994)) are known. However, it is considered more desirable to use human skin itself or grafted human skin which can also reflect the kinetics in the subcutaneous tissue.

As a model system utilizing human skin, a method of performing a single ultraviolet irradiation to a nude mouse (SCID mouse) having human skin grafted thereon is known (Del Bino S, Vioux C, Rossio-Pasquier P, Jomard A, Demarchez M, Asselineau D, Bernerd F, Br. J. Dermatol., 150 (4), 658-67 (2004)). However, since this is not a model in which ultraviolet radiation is continuously irradiated every day for several weeks, and involves ultraviolet irradiation for a short time period, the condition of photodamage in human skin under the effect of long-term irradiation of UVB cannot be sufficiently observed in the model. Thus, there has been established an animal model provided with a photodamaged human skin, which highly approximates photodamage, by continuously irradiating a specific amount of UVB for a specific amount of time (Hachiya A, et al., Am. J. Pathol., 174, 401 (2009)).

Meanwhile, matrix metalloproteinases (MMPs) are enzymes which degrade extracellular matrix proteins such as collagens, elastins and proteoglycans, and are reported to participate in the process of photodamage. It is reported, with regard to photodamaged skin, that disproportion of MMP-1 simultaneously causes loss of collagens I and III due to decreased synthesis of procollagens, as well as degradation of collagens in the dermis (Brennan M, et al., Photochem. Photobiol., 78, 43-48 (2003)). It is also reported that loss of collagens VII and IV at the dermal-epidermal junction is recognized in a skin where photodamage can be seen, and in the experiment using hairless mice, repeated irradiation of UVB induces production of MMP-2 and MMP-9, thus augmenting the degradation of collagens VII and IV (Contet-Audonneau J L, et al., Br. J. Dermatol. 140, 1038-1047 (1999)).

The activity of MMPs is known to be inhibited by tissue inhibitors of metalloproteinases (TIMPs), and a TIMP exhibits its inhibitory action by forming a 1:1 complex with an activated MMP. Therefore, normalizing the balance between the MMP activity and the TIMP activity is considered useful for the prevention of skin aging, and it has been found to date that, for example, an extract of cultured cells of a plant belonging to the genus *Lithospermum* and a caffeic acid polymer have an MMP inhibitory action (Japanese Patent Application Laid-Open (JP-A) No. 2008-31088). Currently, it is known that there are four types of the TIMPs, i.e., TIMP-1, TIMP-2, TIMP-3 and TIMP-4, and the above-mentioned patent document discloses that lithospermic acid has a TIMP-2 activity enhancing action.

JP-A No. 2000-86489 describes that combining retinol and sitosterol results in a decrease in the contents of MMP-1 and MMP-3 that are related to intrinsic aging, and an increase in the content of TIMP-1, but the data presented in the Examples do not necessarily show a decrease in the contents of MMP-1 and MMP-3 in connection with the aforementioned combination, and do not show an increase in the content of TIMP-1. Furthermore, this patent document is not related to photodamage.

In regard to TIMP-1, it has also been reported that a single irradiation of UVB increases the expression level of TIMP-1 mRNA (Brenneisen P, et al., Photochem. Photobiol., 64, 877-885 (1996)), while a single irradiation of UVB does not change the expression level of TIMP-1 protein (Brenneisen P, et al., Biochem. J., 365, 31-40 (2002)).

However, nothing has been known heretofore concerning the influence of the long-term irradiation of UVB on TIMP-1, and the relevance between photodamage of skin and TIMP-1 has not been investigated.

SUMMARY OF THE INVENTION

The present invention provides a method for evaluating or selecting an agent for preventing or curing photodamage of skin, the method including:

(A) contacting cells that are capable of expressing TIMP-1 gene or TIMP-1 protein, with a test substance;

(B) measuring the expression level of the TIMP-1 gene or the TIMP-1 protein in the cells;

(C) comparing the expression level obtained in (B), with the expression level of TIMP-1 gene or TIMP-1 protein in a control group in which the cells capable of expressing TIMP-1 gene or TIMP-1 protein have not been contacted with the test substance; and (D) evaluating or selecting the test substance which increases the expression level of TIMP-1 gene or TIMP-1 protein, as an agent for preventing or curing photodamage of skin, based on the results of (C).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DESCRIPTION OF THE PREFERRED EMBODIMENTS

Figure 1:
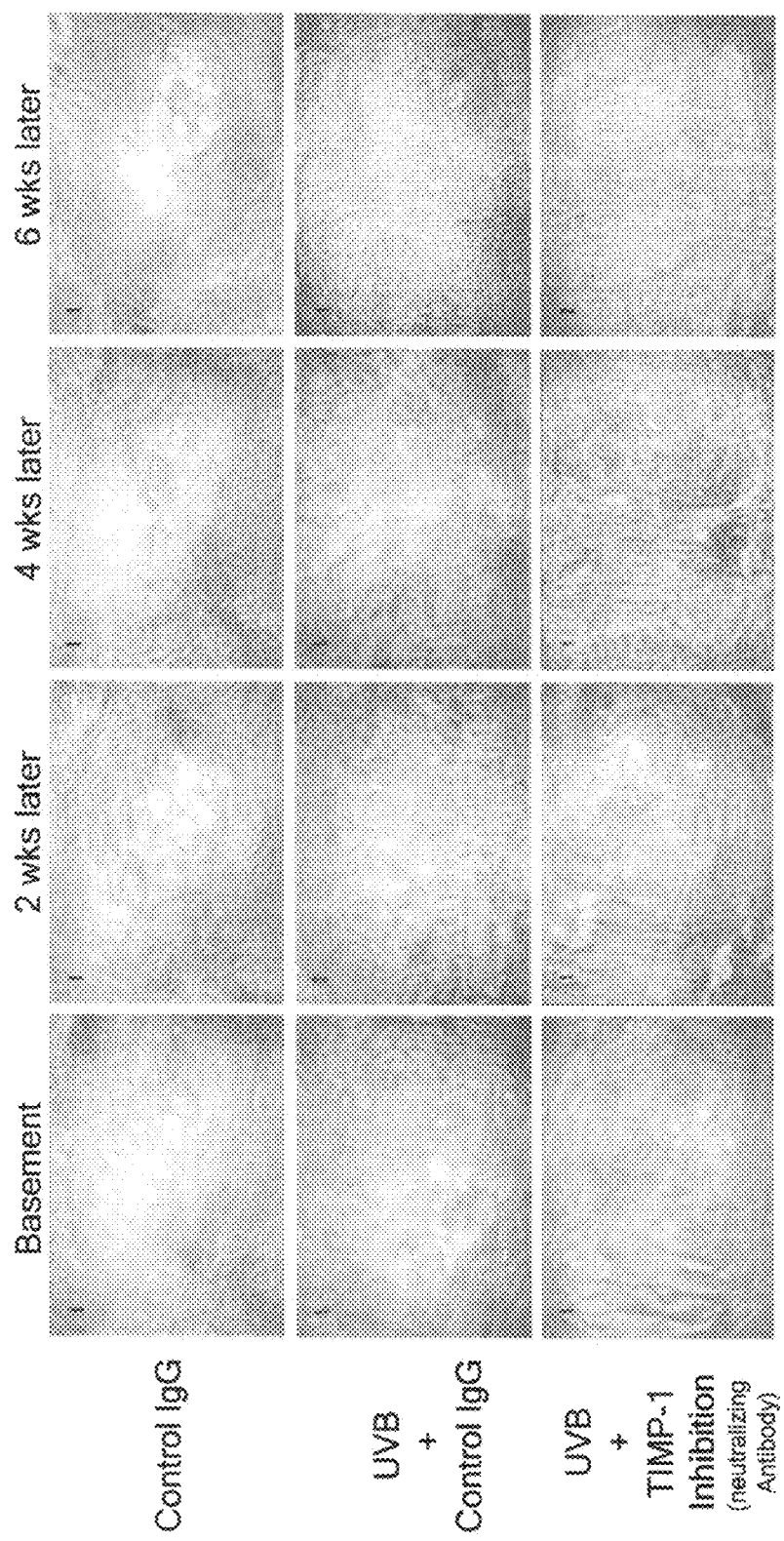
FIG. 1 is a diagram showing the effect of TIMP-1 neutralizing antibody on photodamage of skin, on the basis of changes in skin roughness of the grafted human skin intradermally administered with the TIMP-1 neutralizing antibody. Upper row: Non-specific IgG-administered and ultraviolet-unirradiated group, Middle row: Non-specific IgG-administered and ultraviolet-irradiated group, and Lower row: TIMP-1 neutralizing antibody-administered and ultraviolet-irradiated group.

The present invention provides a method for evaluating or selecting a substance capable of preventing or curing photodamage of skin.

The inventors of the present invention found that among the various types of TIMPs, the expression level of TIMP-2 is lower in the skin of the inner part of the upper arm, which part is less exposed to ultraviolet radiation, while no change is recognized in the expression of TIMP-2 and TIMP-3, with only the expression of TIMP-1 being markedly reduced, in the grafted skin where photodamage has been induced by performing long-term irradiation with UVB. The inventors also found that when a TIMP-1 neutralizing antibody is intradermally administered immediately after irradiating grafted human skin with UVB, roughness of surface of the grafted human skin is increased. Based on these results, it was found that TIMP-1 participates in the prevention and cure of morphological change in photodamaged skin, and if this TIMP-1 production increasing action is used as an index, a substance which is capable of preventing or curing photodamage of skin can be more accurately evaluated or selected.

According to the present invention, the preventive or cure effect of various substances on photodamage (e.g., morphological changes) of skin can be evaluated more accurately and conveniently, and it becomes possible to more accurately select a substance having the preventive or cure effect.

Cells capable of expressing TIMP-1 gene or TIMP-1 protein that are used in the present invention include fibroblasts of mammals, such as skin fibroblasts, lung fibroblasts and gingival fibroblasts, chondrocytes and synoviocytes of mammals and the like. Examples of the mammals include human being, mouse, rat, rabbit and the like. These cells may be cells obtained from primary culture, or cells obtained after repeated subculture and subjected to in vitro aging. Furthermore, the cells may be cells derived from a fetus, or may also be derived from an aged person. These cells may be collected from tissues by a known method and used, or commercially available products may be purchased and used. Among these, human-derived fibroblasts are preferred, and human-derived skin fibroblasts are more preferred.

The contact between the cells and a test substance can be carried out, for example, by preliminarily adding the test substance into a culture fluid to a predetermined concentration, and then introducing the cells into the culture fluid, or by adding the test substance into a culture fluid in which the cells have been introduced, to a predetermined concentration.

Here, the concentration of the cells capable of expressing TIMP-1 gene or TIMP-1 protein at the time of inoculation is preferably $0.5 \times 10^3$ to $1.0 \times 10^5$ cells/well, more preferably $1.0 \times 10^3$ to $3.5 \times 10^4$ cells/well, in the case of using a 24-well plate. The concentration of the test substance is preferably 0.00001 to 10% by mass (residual solid content), more preferably 0.0001 to 3% by mass (residual solid content).

The test substance is not particularly limited as long as it is a substance which is predicted to be able to directly or indirectly exert influence on photodamage of skin. For example, the test substance includes an extract obtained from an animal or a plant, a compound, a chemical substance or the like.

As for the medium in which cells capable of expressing TIMP-1 gene or TIMP-1 protein are cultured, a medium commonly used for culturing the cells can be used. For example, 10% FBS-containing Dulbecco's Modified Eagle's Medium or the like may be included in the medium. At the time of subculturing and during cell proliferation, it is preferable to add a proliferation additive such as a growth factor, an antibacterial agent, insulin, or hydrocortisone to the medium. Subsequently, the culture supernatant is recovered, and the expression level of the TIMP-1 gene or TIMP-1 protein is measured.

Measurement of the expression level of the TIMP-1 gene may be carried out, in the case of detecting in terms of the mRNA level, for example, by extracting total RNA from the cells, and detecting and quantifying the mRNA transcribed from the TIMP-1 gene using a real-time RT-PCR method, an RNase protection assay method, a Northern blot analysis method or the like.

Measurement of the expression level of the TIMP-1 protein can be carried out by a routine immunoassay method. For example, an RIA method, an EIA method, ELISA, a bioassay method, Western blotting or the like can be carried out, among which Western blotting is desirable for being inexpensive and convenient.

For evaluating an agent for preventing or curing photodamage of skin, the expression level of TIMP-1 gene or TIMP-1 protein in the cells capable of expressing the TIMP-1 gene or TIMP-1 protein and having been contacted with a test substance is compared with the expression level in a control group (control cells) which has not been contacted with the test substance. When the expression level in the cells which have been contacted with the test substance is increased compared to that in the control group, the test substance can be evaluated to have an effect of preventing or curing photodamage of skin, and such substance can be selected. A substance thus evaluated or selected can be used as a pharmaceutical product or the like which is useful for preventing or curing photodamage of skin, such as decreased elasticity and looseness of skin, or increased roughness of skin surface.

EXAMPLES

Test Example 1

Investigation of Changes in Morphological Changes in Grafted Skin After Intradermal Administration of TIMP-1 Neutralizing Antibody (1) Grafting of Abdominal Skin Onto Severe Combined Immunodeficient (SCID) Mouse The abdominal skin of a Caucasian woman (age 41), which was obtained from abdominoplasty surgery performed at University Hospital in Cincinnati (Cincinnati, Ohio), was trimmed to an appropriate size (about 2.0 cm×2.0 cm to about 3.0 cm×3.0 cm) and was washed with phosphate buffered saline (PBS). Subsequently, the specimen was preserved until grafting, while being immersed in Dulbecco's Modified Eagle's Medium (DMEM) containing L-glutamine and antibiotic/antimycotic (Invitrogen, Inc.). Four- to six-week old female SCID mice (Taconic Farms, Inc., NY) which had been acclimated for about one week, were shaved on the dorsal side at the animal facility at Cincinnati Children's Hospital Research Foundation (Cincinnati, Ohio), and then were anesthetized in a box containing isofluorane/oxygen (3%/0.8 liter). Subsequently, while aspirating isofluorane/oxygen (2%/0.7 liter), the dorsal skin of the mice was excised (diameter about 2 to 3 cm), and the human abdominal skin was sutured to the mouse skin. The boundaries between the grafted abdominal skin and the mouse skin were subjected to sensory denervation by adding sensor caine. After the grafting, the mice were maintained at 37° C. for one hour or until the mice recovered from anesthesia.

(2) Photodamage Induced by Chronic UVB Irradiation of Grafted Human Abdominal Skin, and Intradermal Administration of TIMP-1 Neutralizing Antibody At a time point after a lapse of 10 weeks from the grafting, at which point the grafted abdominal skin had undergone complete agglutination, photodamage was induced in the grafted human skin by the method shown by Hachiya et al. (Hachiya A, et al., Am. J. Pathol., 174, 401 (2009)). That is, irradiation was started using UVB lamps (34-0044-01 lamps, UVB, Upland, Calif.) equipped with a filter which allows irradiance of UVB with a peak at 302 nm. The amount of UVB energy was measured using a UV light meter, UV-340MSR7000 (LutronElectronic Enterprise Co., Ltd., Taiwan). The distance from the filter to the surface of the grafted skin was securely maintained at about 30 cm, and for the first one week, UVB was irradiated at a dose of 40 $mJ/cm^2$, which was equivalent to 1 minimal erythema dose (MED). The irradiance level was increased by 10 $mJ/cm^2$ until the end of the third week, and thereafter, the level was maintained at 60 $mJ/cm^2$ until the end of the sixth week. Since the irradiation was maintained for 5 days per week, the total irradiance level of UVB was 1.65 $J/cm^2$. During the period of UVB irradiation, the mice were allowed to freely move around in a transparent container having a bottom area of about 100 $cm^2$. Furthermore, intradermal administration of a TIMP-1 neutralizing antibody was carried out every other day, immediately after irradiating UVB. The concentration for administration was set at 20 μg/mL, which was equivalent to four times the concentration used in Reed M J, et al., Microvasc. Res., 65, 9 (2003).

(3) Results

The changes in morphological changes induced on the grafted abdominal skin by UVB irradiation were visually observed. In the group which was not irradiated with UVB and non-specific IgG was intradermally administered to (upper row in FIG. 1), no significant changes in the appearance were recognized, while in the group which was continuously irradiated with UVB and non-specific IgG was intradermally administered to, rough structures on the surface of the skin were firstly observed at 4 weeks after, and became obvious at 6 weeks after from the continuous irradiation (middle row in FIG. 1). On the other hand, in the group which was continuously irradiated with UVB and a TIMP-1 neutralizing antibody was intradermally administered to (lower row in FIG. 1), increased roughness of skin surface was observed at 4 weeks after from the continuous irradiation, which was earlier than the group which was continuously irradiated with UVB and non-specific IgG was intradermally administered to. Furthermore, conspicuous desquamation was also observed as well as the increased roughness of skin surface.

Test Example 2

Investigation of the Expression Level of TIMPs mRNA in Skin (1) Expression of Various TIMPs in Ultraviolet-Unirradiated Skin The skin of the inner part of the upper arm collected from Caucasian women in their twenties and fifties by punch biopsy, was purchased from Stephens & Associates, Inc. (Carrollton, Tex.), a contract laboratory in Dallas. Total RNA was extracted from a portion of the skin samples according to a commonly used method. After cDNAs were produced, a quantitative analysis of gene expression was performed for TIMP-1, TIMP-2 and TIMP-3 using specific probes and a 7300 Real Time PCR System (Applied Biosystems, Inc.). The expression of RPLP0 was utilized as the internal standard for the analysis of gene expression.

(2) Expression of Various TIMPs After Ultraviolet Irradiation

Continuous irradiation for 6 weeks (40 to 60 $mJ/cm^2$) was carried out on the human skin collected in section (1) above, and 24 hours after the final irradiation, total RNA was extracted. After cDNAs were produced, a quantitative analysis of gene expression was performed for TIMP-1, TIMP-2 and TIMP-3 using specific probes and a 7300 Real Time PCR System (Applied Biosystems, Inc.). The expression of RPLP0 was utilized as the internal standard for the analysis of gene expression, in the same manner as described above.

(3) Results

Figure 2:
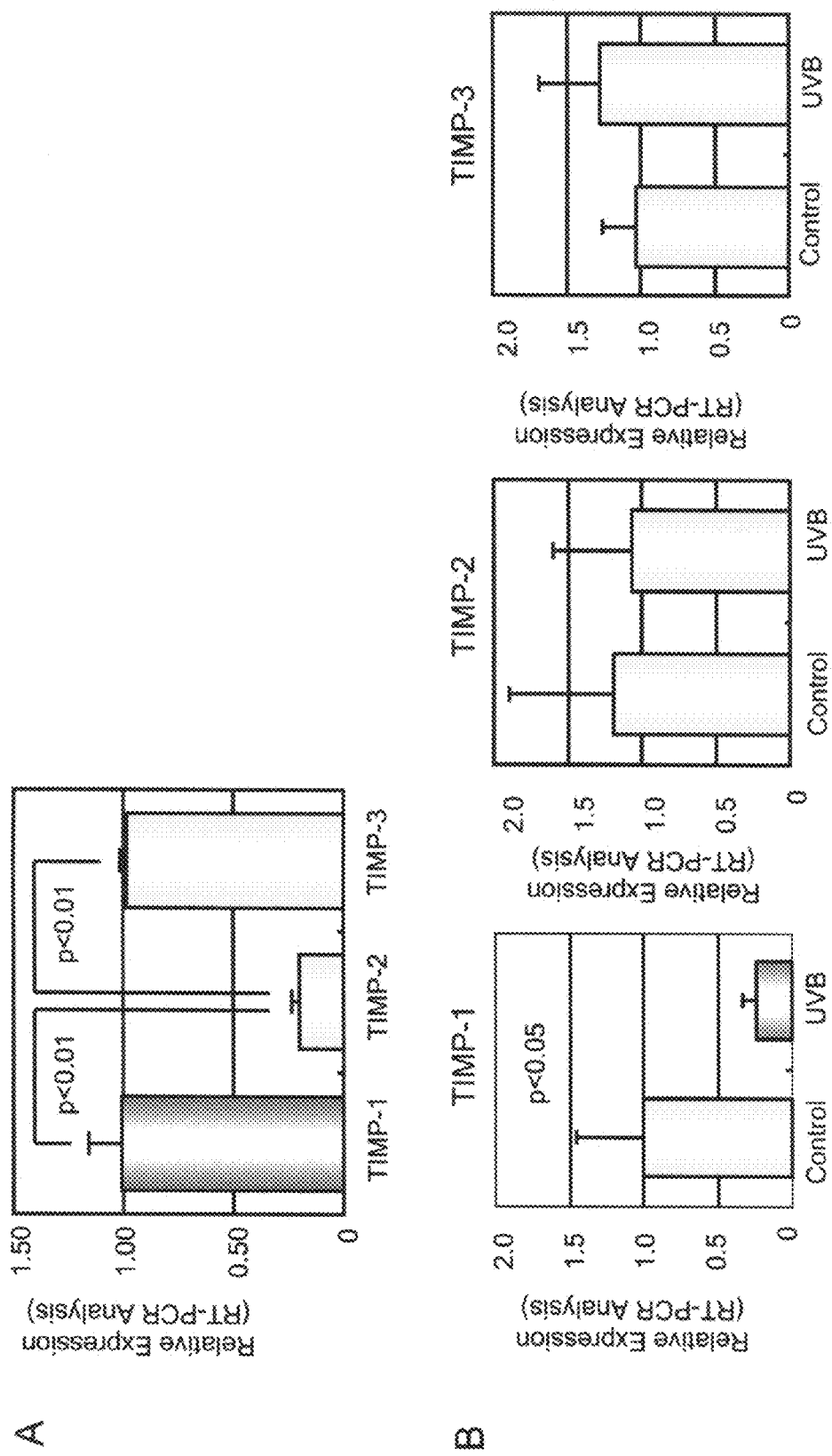
FIG. 2 is a diagram showing the expression of TIMPs mRNA: (A) Relative ratio of the expression level of TIMP in ultraviolet-unirradiated skin of the inner part of the upper arm; and (B) Changes in the expression level of TIMPs after ultraviolet irradiation in the grafted human skin.

The relative expression levels of TIMP-1, TIMP-2 and TIMP-3 were analyzed using the total RNA derived from the skin of the inner part of the upper arm. The ratio of the expression level was 5:1:5 (1:0.2:1) (FIG. 2A).

Furthermore, a comparison was made for the gene expression level of TIMP-1, TIMP-2 and TIMP-3 between a photodamaged skin model and a UVB-unirradiated grafted skin. While the expression of TIMP-1 was markedly reduced in the case of photodamage induced by chronic UVB irradiation, no change was recognized in the expression of TIMP-2 and TIMP-3 even upon photodamage (FIG. 2B).

From the results described above, it was conceived that a marked decrease in the expression of TIMP-1, even among various TIMPs, contributes particularly to the enhancement of photodamage.

Test Example 3

Screening of Agent for Preventing or Curing Photodamage of Skin (1) Method

Figure 3:
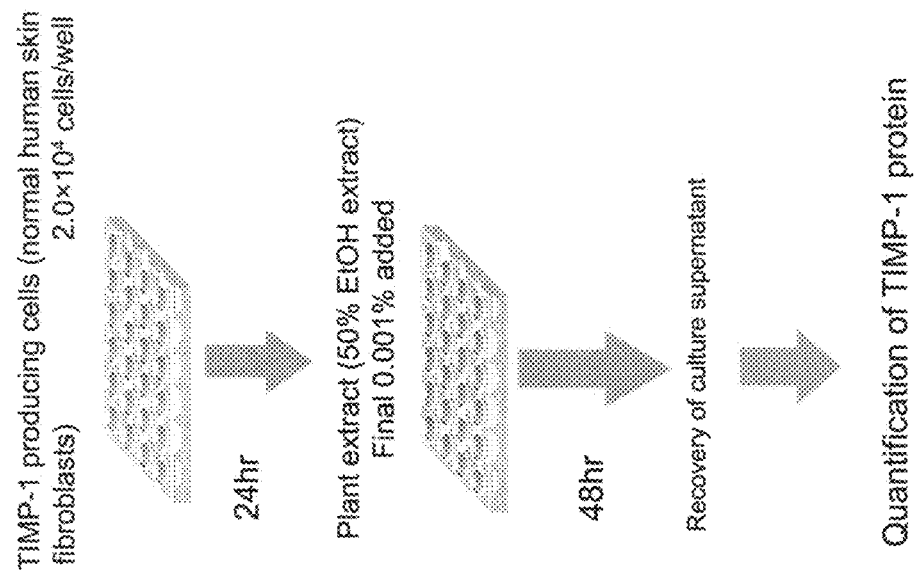
FIG. 3 is a diagram showing an outline of the method of screening an agent for preventing or curing photodamage of skin.

An outline of the present screening method is presented in FIG. 3. In short, normal human skin fibroblasts were inoculated onto a 24-well plate at a cell density of $2 \times 10^4$ cells/well, and culture was started using 0.5 mL of 10% FBS-containing DMEM (Sigma Aldrich Company). After 24 hours, the medium was replaced with 0.5 mL of a serum-free medium, and various plant extracts (50% EtOH extract products) were added as test substances. The concentration of the extracts added was 0.001% (residual solid concentration), or an equal amount of 50% EtOH was added as a control. After 48 hours from the addition of the extracts, the medium and the cells were respectively recovered as measurement samples. The medium was recovered directly from each well, and then centrifuged for 2 minutes at 12,000 rpm, and the amount of TIMP-1 protein in the supernatant was measured using a human TIMP-1 assay system (GE Healthcare Biosciences, Inc.).

Furthermore, after recovering the medium from each well, the cells were washed two times with 0.5 mL of PBS, 125 μL of 0.1 N NaOH was added, and the cells were lysed for about 5 minutes at room temperature. The resultant was recovered as a cell lysate. The amount of proteins in the cell lysate was measured using a BCA Protein Assay Kit (Pierce), and thereby the toxicity of the various plant extracts added was evaluated.

(2) Results

An evaluation was performed on the effects of various plant extracts (extraction solvent 50% EtOH) on the production of TIMP-1. In the sample treated with a *perilla* extract or a *Mentha piperita* extract, the amount of TIMP-1 protein was increased to 2.0 times or more relative to the control (Table 1). Samples in which the ratio of the amount of protein with respect to the control (added with 50% EtOH) was 0.5 or less, were excluded. None of the plant extracts exhibited cytotoxicity.

The *perilla* extract is already known as a photoaging inhibitor (JP-A No. 2002-104924), and *Mentha piperita* extract (peppermint) is known as a collagenase (MMP-1) inhibitor (JP-A No. 2000-159631).

From these results, it was indicated that a substance having a preventive or cure effect on photodamage can be evaluated or selected using the TIMP-1 production increasing action as an index.

TABLE 1

| Plant extract | Expression level of TIMP-1 (relative to control) |
|---|---|
| *Perilla* | 2.26 |
| *Mentha piperita* | 2.38 |

What is claimed is:

1. A method for evaluating or selecting an agent that decreases UVB-induced photodamage of skin that is enhanced by a decrease in TIMP-1 gene or TIMP-1 protein expression in said skin, the method comprising:
    (A) contacting mammalian skin cells that are capable of expressing the TIMP-1 and TIMP-2-genes or proteins with a test substance;
    (B) measuring the expression level of the TIMP-1 and TIMP-2 genes or proteins in the skin cells;
    (C) comparing the expression level of said TIMP-1 and TIMP-2 genes or proteins obtained in part (B), with the expression level of said TIMP-1 and TIMP-2 genes or proteins in a control group in which said skin cells have not been contacted with the test substance; and
    (D) based on the results of part (C), evaluating or selecting a test substance that increases the expression level of the TIMP-1 gene or TIMP-1 protein over that of the control group but does not change the expression level of TIMP-2 gene or protein, as an agent that can reduce said UVB-induced photodamage of skin that is enhanced by a decrease in TIMP-1 gene or TIMP-1 protein expression in said skin.

2. The method of claim 1, wherein said mammalian skin cells are human skin cells.

3. The method of claim 1 or 2, wherein said skin cells are in culture.

4. The method of claim 1, wherein said expression level of said TIMP-1 and TIMP-2 genes is evaluated.

5. The method of claim 4, wherein said expression level of said TIMP-1 and TIMP-2 genes is evaluated by detecting TIMP-1 and TIMP-2 mRNA.

6. A method for evaluating or selecting an agent that decreases UVB-induced photodamage of skin that is enhanced by a decrease in TIMP-1 gene or TIMP-1 protein expression in said skin, the method comprising:
    (A) contacting skin cells that are capable of expressing the TIMP-1 and TIMP-2 genes or proteins with a test substance;
    (B) measuring the expression level of the TIMP-1 and TIMP-2 genes or proteins in the skin cells;
    (C) comparing the expression level obtained in part (B), with the expression level of the TIMP-1 and TIMP-2 genes or proteins in a control group in which the skin cells have not been contacted with the test substance; and
    (D) based on the results of part (C), evaluating or selecting a test substance that increases the expression level of the TIMP-1 gene or TIMP-1 protein over that in the control group but does not change the expression level of TIMP-2 gene or protein, as an agent that can reduce said UVB-induced photodamage of skin that is enhanced by a decrease in TIMP-1 gene or TIMP-1 protein expression in said skin.

7. The method of claim 6, wherein said skin cells are cells derived from skin tissue of an animal.

8. The method of claim 6, wherein said skin cells are skin cells grafted to an immunodeficient mouse.

9. The method of any one of claims 6-8, wherein said skin cells are human skin cells.

10. The method of claim 2, wherein said human skin cells are human skin fibroblasts.

* * * * *